(12) United States Patent
Weisenberger

(10) Patent No.: US 6,317,622 B1
(45) Date of Patent: Nov. 13, 2001

(54) GAMMA-RAY BLIND BETA PARTICLE PROBE

(75) Inventor: Andrew G. Weisenberger, Grafton, VA (US)

(73) Assignee: Southeastern University Research Assn., Newport News, VA (US)

(*) Notice: Subject to any disclaimer, the term of this patent is extended or adjusted under 35 U.S.C. 154(b) by 0 days.

(21) Appl. No.: 09/201,178

(22) Filed: Nov. 30, 1998

(51) Int. Cl.$^7$ ............................................. A61B 6/00
(52) U.S. Cl. ................................................ 600/431
(58) Field of Search ............................. 250/207, 336.1, 250/396 R, 399, 306, 307, 308, 440.11; 376/159, 157; 600/407, 431

(56) References Cited

U.S. PATENT DOCUMENTS

| | | |
|---|---|---|
| 3,609,353 * | 9/1971 | Paine .................................. 250/336.1 |
| 5,008,546 | 4/1991 | Mazziota et al. . |
| 5,325,855 | 7/1994 | Daghighian et al. . |
| 5,338,937 | 8/1994 | Daghighian et al. . |
| 5,744,805 | 4/1998 | Raylman et al. . |
| 5,753,917 | 5/1998 | Engdahl . |

* cited by examiner

Primary Examiner—George Manuel

(57) ABSTRACT

An intra-operative beta particle probe is provided by placing a suitable photomultipler tube (PMT), micro channel plate (MCP) or other electron multiplier device within a vacuum housing equipped with: 1) an appropriate beta particle permeable window; and 2) electron detection circuitry. Beta particles emitted in the immediate vicinity of the probe window will be received by the electron multiplier device and amplified to produce a detectable signal. Such a device is useful as a gamma insensitive, intra-operative, beta particle probe in surgeries where the patient has been injected with a beta emitting radiopharmaceutical. The method of use of such a device is also described, as is a position sensitive such device.

5 Claims, 1 Drawing Sheet

GAMMA-RAY BLIND BETA PARTICLE PROBE

The United States of America may have certain rights to this invention under Management and Operating Contract No. DE-AC05-84ER 40150 from the Department of Energy.

FIELD OF THE INVENTION

The present invention relates to probes for the detection of beta particles, and more specifically to beta particle probes which are blind to gamma-rays present in the area of detection.

BACKGROUND OF THE INVENTION

The use of intra-operative probes to assist surgeons in defining the boundaries of cancerous lesion during surgical procedures performed following the injection of the patient with a radiopharmaceutical such as a positron labeled fluorodeoxyglucose (FDG) or similar materials is becoming more and more commonplace. The problem of detecting the relatively weak beta signal from tissue in the vicinity of a probe inserted into the proximity of the lesion from the relatively strong gamma background field emitted from other regions of the body remains, however, perplexing. Furthermore, it has been discovered that positron emitting radiopharmaceuticals such as FDG create two high energy gamma rays or photons when the positron collides with an electron. The presence of these highly penetrating gamma rays greatly reduces the observed lesion-to-background contrast hoped to be gained by the use of these radiopharmaceuticals when conventional prior art techniques and systems are used in an attempt to detect the beta particles. It would therefore be highly desirable to have a small probe useful for intra-operative procedures that is highly sensitive to beta emissions while being insensitive or relatively so to gamma radiation.

As a consequence, a number of solutions have been proposed to solve this problem. For example, U.S. Pat. No. 5,744,805 to Raylman et.al. proposes the use of a probe system that utilzes an ion-implanted silicon charged-particle detector for generating an electrical signal in response to received beta particles.

U.S. Pat. No. 5,008,546 to Mazziotta et. al. discloses a probe comprised of two plastic scintillators, in a photocathode, optically coupled to corresponding light pipes. One of the plastic scintillators is shielded against beta radiation while the other is left to detect both beta and gamma radiation. The gamma radiation sensitivity of the two probes is empirically established and used as a weighted factor to subtract the outputs of the two probes to leave a signal indicative of the beta radiation emitted by the radiolabeled tissue.

U.S. Pat. No. 5,753,917 to Engdahl, although not directed specifically at the design of an intra-operative probe, describes a so-called phoswich or scintillation crystal assembly having multiple crystal layers for interacting with various photon or gamma ray energy levels so as to distinguish therebetween.

The interoperative probe of the present invention utilizes a significantly different approach to the problem of gamma ray interference with beta particle measurement that relies on a beta particle probe that is blind to gamma radiation, and hence, uninfluenced thereby in the detection process.

Secondary electron amplifiers have long been used in combination with the aforesaid scintillators to enhance the output of scintillator materials, or photocathodes, excited by gamma or other similar high energy emissions. Similarly, secondary electron multipliers have been used alone for the detection of beta particles. Some such devices are commonly referred to as photomultiplier tubes (PMT) or microchannel plates (MCP). Fundamentally, these devices comprise one or a series of dynodes which, when impacted by a beta particle, generally an electron, produce a shower of electrons thereby amplifying the number of particles available for detection. A variety of such devices have been designed, including flat plates, and "Chevron" devices that comprise layers of angularly displaced dynodes. Such devices are well known in the art and have broad usage in a number of electron and beta sensing and amplification devices.

The use of such devices for the detection of beta particles, however, has always required placement of the beta emitting sample under evaluation or the beta producer, in the case of a scintillator, into the vacuum with the PMT or MCP device to assure minimization of interference from air or gas between the source of the beta particle and the amplifier.

SUMMARY OF THE INVENTION

It has now been discovered that a highly useful and effective beta particle probe can be provided by placing a suitable PMT, MCP or other electron multiplier device within a vacuum housing equipped with an appropriate beta particle permeable window and electron detection circuitry, in the absence of a photocathode or any other material that responds to gamma radiation. In this instance, the beta particle source is external to the PMT or MCP vacuum chamber and yet beta particles emitted in the immediate vicinity of the probe window will be received by the PMT or MCP and amplified to produce a detectable signal Such a device is useful as a gamma insensitive, intra-operative, beta particle probe in surgeries where the patient has been injected with one of the aforementioned beta emitting radiopharmaceuticals. A position sensitive such device is also described.

DETAILED DESCRIPTION OF THE INVENTION

Figure 1:
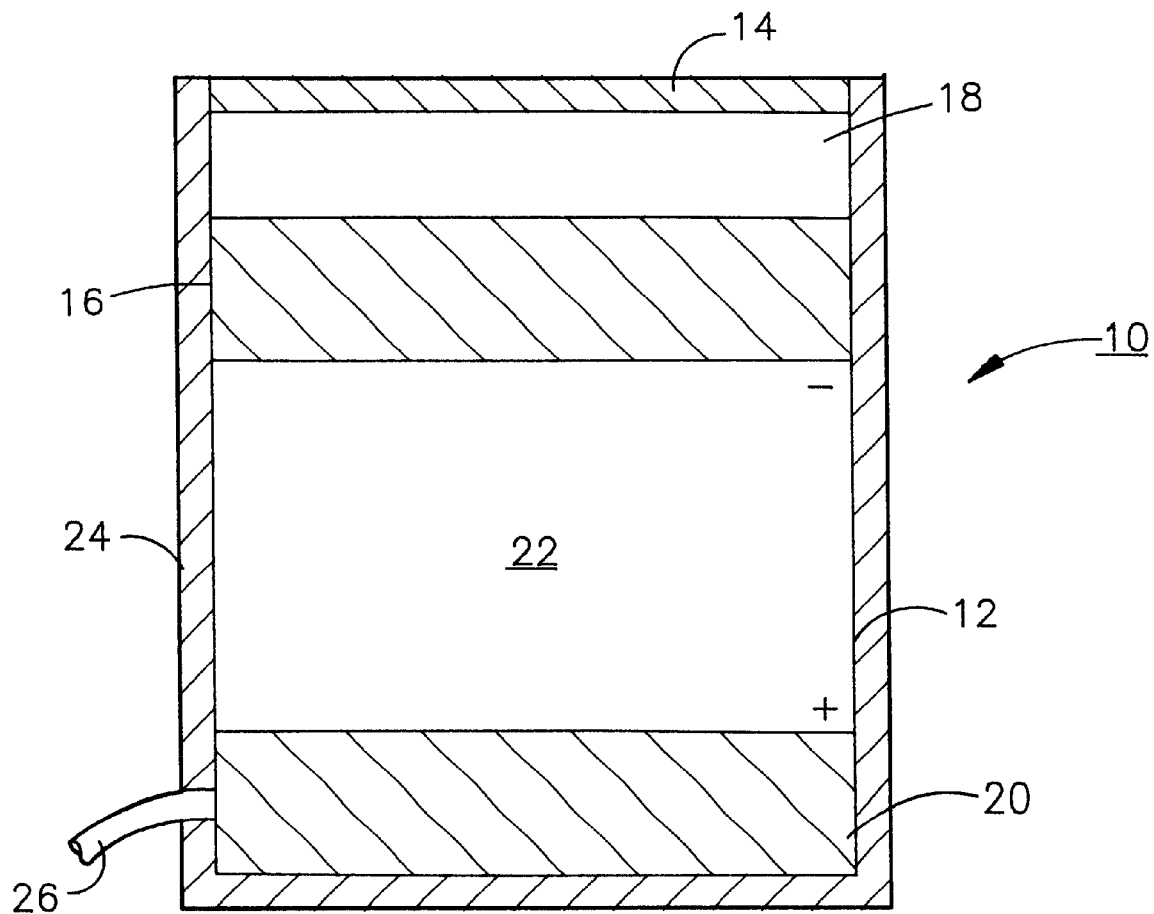
FIG. 1 is a schematic drawing of a beta particle probe in accordance with the present invention.

As shown in FIG. 1, the probe of the present invention 10 comprises a vacuum housing 12 having a beta particle permeable window 14 at one end thereof. Behind beta particle permeable window 14 is an electron multiplier 16. In the case shown in FIG. 1, a gap 18 has been shown between beta particle window 14 and electron multiplier 16, however, this gap is not necessary, but may be provided for simplicity of assembly or otherwise, but preferably, is eliminated entirely. Appropriate electron detection circuitry 20 is located at the opposite end of vacuum housing 12 from beta particle permeable window 14. The interior 22 of vacuum housing 12 is evacuated, i.e. under a vacuum of at least about $1-1.5 \times 10^{6-}$ Torr. Vacuums on the order of those used in conventional PMT and MCP devices are adequate for the purposes of this invention. In order to prevent the possibility of electrical shock to either the patient or the physician user of the probe, a preferably low mass insulation layer 24 preferably covers the outer surface of vacuum housing 12. Appropriate polymeric and rubber based products are well known for this purpose.

Vacuum housing 12 may be constructed of any suitable material of the type used for the housings of secondary electron multiplier devices. Metals, such as steel or aluminum are entirely suitable, so long as they are capable of maintaining the required vacuum within vacuum housing 12, while not otherwise interfering with the desired beta particle detection and measurement.

Beta particle permeable window 14 of probe 10 may be of any suitable beta particle permeable material which is concurrently capable of structurally resisting the vacuum at the interior of vacuum housing 12. Titanium, on the order of from about 5 to about 50$\mu$ in thickness, has been found suitable for this application. However glass, other metals etc. which are permeable, i.e. offer no significant obstruction to the passage of or significant undesirable interaction with beta particles traversing beta particle permeable window 14, can be used.

While FIG. 1 shows a gap 18, because of the relatively low energy of beta particles, it is preferred that that electron multiplier 16 be located as close to window 14 as possible to achieve the highest possible sensitivity to incoming beta radiation.

Electron multiplier 16 can comprise any of a number of commercially available or specially designed such devices which comprise one or more plates or other elements, i.e. dynodes which receive incoming electrons and emit an increased number of electrons according to well known methods. Such devices are commercially available from Galileo Electro-Optics Corporation, Galileo Park, Sturbridge, Mass. as well as Amperex Eletronic Corporation, 230 Duffy Ave., Hicksville, N.Y.

Of course, vacuum housing 12 must be equipped with an appropriate electrical field to assure that both the primary received beta particles and the secondary electrons produced by electron multiplier 16 migrate in the correct direction toward electron detection circuitry 20. This requires that that portion of vacuum container 12 that holds detection circuitry 20, be the anode of the internal electrical field, as shown in FIG. 1. The design and implementation of such fields, in such devices, is well within the skill of the art, as is the design and incorporation of the charge sensitive detection circuitry appropriate for electron detection in this application.

For surgical use, the probe of the present invention, must, of course, be suitable for intra-operative use, i.e. it must be small (~1–10 $cm_2$ in cross section), maneuverable, i.e. located at the end of a suitable cable 26 which connects to appropriate display and alarm circuitry remote from the probe, and rugged, to withstand the necessary sterilization and handling procedures that occur in the operating environment. For use in other non-surgical applications, the probe of the present invention may, of course, take on any dimensions suitable for those applications.

In use, the probe of the present invention is utilized in a surgical procedure wherein the patient has been previously injected with an appropriate beta emitting isotope, such as FDG, that is preferentially absorbed in metabolism by the cancerous lesion undergoing resection. Once the visual detectable lesion portion has been removed, the surgeon brings the beta particle permeable window 14 of probe 10 of the present invention into contact with the suspect remaining tissue. Since beta particles can travel only very short distances, on the order of 1–2 mm, in tissue, an indication of the presence of significant beta particle emission, through a visual or audible alarm system, provides to the surgeon an indication that remaining cancerous tissue is present. When resection has occurred to the point where beta detection is negligible, the surgeon has confidence that an appropriate level of resection has been performed and that further removal of tissue is unnecessary.

Because of the short distance traveled by the beta particles between the tissue and the detector, the probe is effectively self-collimating, since minimal electron scattering will occur between the tissue and the probe/detector. According to another embodiment of the present invention, a layer of secondary emissive material such as germanium, alumina with molybdenum or MgO and KCI is coated on the inside surface of window 14 to obtain minimum dispersion or decay of beta particles prior to the onset of amplification.

Position readout in such a device can be obtained by the use of discreet anodes, cross wire anodes or via a resistive anode. Position sensitive PMT and MCP electron multiplier devices are commercially available from the aforementioned suppliers and can be readily incorporated into such a device for purposes of obtaining positional information when necessary.

From the foregoing description, one skilled in the art can easily ascertain the essential characteristics of this invention, and without departing from the spirit and scope thereof, make various changes and modifications of the invention to adapt it to various usages and condition. It is therefore intended that the scope of the invention is limited only by the scope of the appended claims.

What is claimed is:

1. A method for the detection of cancerous tissue during an operative procedure for the removal thereof comprising:

injecting a patient undergoing cancer removal surgery with an appropriate beta emitting radiopharmaceutical; and determining the presence or absence of cancerous tissue in an area under surgery by contacting said tissue with a gamma insensitive beat particle probe comprising:
a) a vacuum housing having first and second ends;
b) a beta particle permeable window forming one of said ends;
c) an electron multiplier within said vacuum housing proximate said beta particle permeable window;
d) electron detection circuitry at the other of said ends and within said vacuum housing;
e) an electrical field designed to induce movement of beta particles and secondary electrons generated by said electron multiplier from said beta particle permeable window to said electron detection circuitry within said vacuum housing; and
f) a display mechanism connected to said beat particle probe.

2. The method of claim 1 wherein said vacuum housing contains no photocathode or other gamma radiation sensitive material.

3. A gamma radiation insensitive beta particle probe comprising:

a vacuum housing containing no photocathode or other gamma radiation sensitive material and having first and second ends;

a titanium beta particle permeable window forming one of said ends;

an electron multiplier within said vacuum housing proximate said beta particle permeable window;

electron detection circuitry at the other of said ends and within said vacuum housing; and an electrical field designed to induce movement of beta particles and secondary electrons generated by said electron multiplier from said beta particle permeable window to said electron detection circuitry within said vacuum housing.

4. A gamma radiation insensitive beta particle probe having an overall cross-section of from about 1 to about 10 square centimeters and comprising:

a vacuum housing containing no photocathode or other gamma radiation sensitive material and having first and second ends;

a titanium beta particle permeable window forming one of said ends;

an electron multiplier within said vacuum housing proximate said beta particle permeable window;

electron detection circuitry at the other of said ends and within mid vacuum housing;

an electrical field designed to induce movement of beta particles and secondary electrons generated by said electron multiplier from said beta particle permeable window to said electron detection circuitry within said vacuum housing; and a cable connecting said beta particle probe to alarm or display circuitry.

5. A gamma radiation insensitive beta particle probe comprising:

a vacuum housing containing no photocathode or other gamma radiation sensitive material and having first and second ends;

a beta particle permeable window forming one of said ends and having a front surface which faces outward from said vacuum housing and a rear surface that faces inward toward said vacuum housing, said rear surface being coated with a secondary emissive material selected from the group consisting of germanium, alumina with molybdenum and a mixture of magnesium oxide and potassium chloride;

an electron multiplier within said vacuum housing proximate said beta particle permeable window;

electron detection circuitry at the other of said ends and within said vacuum housing; and an electrical field designed to induce movement of beta particles and secondary electrons generated by said electron multiplier from said beta particle permeable window to said electron detection circuitry within said vacuum housing.

* * * * *